(12) United States Patent
Benson

(10) Patent No.: US 10,342,992 B2
(45) Date of Patent: Jul. 9, 2019

(54) ORIENTING A BRACHYTHERAPY APPLICATOR

(75) Inventor: Maria Benson, West Boylston, MA (US)

(73) Assignee: HOLOGIC, INC., Marlborough, MA (US)

( * ) Notice: Subject to any disclaimer, the term of this patent is extended or adjusted under 35 U.S.C. 154(b) by 1841 days.

(21) Appl. No.: 12/985,401

(22) Filed: Jan. 6, 2011

(65) Prior Publication Data

US 2012/0178983 A1 Jul. 12, 2012

(51) Int. Cl.
*A61M 36/00* (2006.01)
*A61N 5/10* (2006.01)

(52) U.S. Cl.
CPC .................................. *A61N 5/1015* (2013.01)

(58) Field of Classification Search
CPC ...... A61N 5/00; A61N 5/1016; A61N 5/1014; A61N 5/1002; A61N 5/1015; A61N 7/022; A61B 5/6852; A61B 5/6853
USPC ................... 600/1–7; 128/897–899
See application file for complete search history.

(56) References Cited

U.S. PATENT DOCUMENTS

| 3,324,847 | A | 6/1967 | Zoumboulis |
| 3,502,878 | A | 3/1970 | Stewart |
| 3,863,073 | A | 1/1975 | Wagner |
| 3,872,856 | A | 3/1975 | Clayton |
| 3,971,950 | A | 7/1976 | Evans et al. |

(Continued)

FOREIGN PATENT DOCUMENTS

| DE | 2539553 | 3/1977 |
| EP | 0340881 | 10/1992 |

(Continued)

OTHER PUBLICATIONS

"Essentials for life: Senographe Essential Full-Field Digital Mammography system", GE Health-care Brochure, MM-0132-05.06-EN-US, 2006, 12 pgs.

(Continued)

*Primary Examiner* — Navin Natnithithadha
*Assistant Examiner* — Sunita Reddy

(57) ABSTRACT

A device for orienting a brachytherapy applicator implanted in a treatment cavity may include an elongated body defining an open channel adapted for slidably receiving at least a portion of a shaft or catheter body of a brachytherapy applicator. A manually engageable gripping element at an end of the elongated body is actuated to constrict at least a portion of the channel around a portion of the shaft to help prevent shaft twist and rotational movement between the elongated body and brachytherapy applicator. At least one engaging element on the elongated body is actuated to releasably engage at least one corresponding engaging element on a brachytherapy applicator. Shaft twist and rotational discontinuity between the elongated body and brachytherapy applicator are further prevented when the at least one engaging element of the elongated body engages the at least one corresponding element of the brachytherapy applicator. The device can advantageously be mounted and removed while the applicator is inside the treatment cavity. Furthermore, the device is an "external tool" that engages the brachytherapy applicator externally about its outer surface.

13 Claims, 11 Drawing Sheets

(56) References Cited

U.S. PATENT DOCUMENTS

| | | |
|---|---|---|
| 3,975,350 A | 8/1976 | Hudgin et al. |
| 4,119,094 A | 10/1978 | Micklus et al. |
| 4,160,906 A | 7/1979 | Daniels et al. |
| 4,310,766 A | 1/1982 | Finkenzeller et al. |
| 4,350,169 A | 9/1982 | Dutcher et al. |
| 4,417,576 A | 11/1983 | Baran |
| 4,454,106 A | 6/1984 | Gansow et al. |
| 4,496,557 A | 1/1985 | Malen et al. |
| 4,559,641 A | 12/1985 | Caugant et al. |
| 4,571,241 A | 2/1986 | Christopher |
| 4,690,677 A | 9/1987 | Erb |
| 4,706,269 A | 11/1987 | Reina et al. |
| 4,706,652 A | 11/1987 | Horowitz |
| 4,744,099 A | 5/1988 | Huettenrauch et al. |
| 4,754,745 A | 7/1988 | Horowitz |
| 4,763,642 A | 8/1988 | Horowitz |
| 4,773,086 A | 9/1988 | Fujita et al. |
| 4,773,087 A | 9/1988 | Plewes |
| 4,819,258 A | 4/1989 | Kleinman et al. |
| 4,821,725 A | 4/1989 | Azam et al. |
| 4,821,727 A | 4/1989 | Levene et al. |
| 4,867,741 A | 9/1989 | Portnoy |
| 4,929,470 A | 5/1990 | Rittenhouse et al. |
| 4,969,174 A | 11/1990 | Scheid et al. |
| 4,989,227 A | 1/1991 | Tirelli et al. |
| 4,998,917 A | 3/1991 | Geiser et al. |
| 4,998,930 A | 3/1991 | Lundahl |
| 5,015,247 A | 5/1991 | Michaelson |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,059,166 A | 10/1991 | Fischell et al. |
| 5,078,142 A | 1/1992 | Siczek et al. |
| 5,084,001 A | 1/1992 | Vant Hooft et al. |
| 5,084,015 A | 1/1992 | Moriuchi |
| 5,084,022 A | 1/1992 | Claude |
| 5,106,360 A | 4/1992 | Ishiwara et al. |
| 5,112,303 A | 5/1992 | Pudenz et al. |
| 5,152,747 A | 10/1992 | Olivier |
| 5,163,075 A | 11/1992 | Lubinsky et al. |
| 5,164,976 A | 11/1992 | Scheid et al. |
| 5,167,622 A | 12/1992 | Muto |
| 5,199,056 A | 3/1993 | Darrah |
| 5,199,939 A | 4/1993 | Dake et al. |
| 5,227,969 A | 7/1993 | Waggener et al. |
| 5,236,410 A | 8/1993 | Granov et al. |
| 5,240,011 A | 8/1993 | Assa |
| 5,259,847 A | 11/1993 | Trambert |
| 5,289,520 A | 2/1994 | Pellegrino et al. |
| 5,302,168 A | 4/1994 | Hess |
| 5,312,356 A | 5/1994 | Engelson et al. |
| 5,314,518 A | 5/1994 | Ito et al. |
| 5,336,178 A | 8/1994 | Kaplan et al. |
| 5,342,305 A | 8/1994 | Shonk |
| 5,359,637 A | 10/1994 | Webber |
| 5,365,562 A | 11/1994 | Toker |
| 5,381,504 A | 1/1995 | Novack et al. |
| 5,411,466 A | 5/1995 | Hess |
| 5,415,169 A | 5/1995 | Siczek et al. |
| 5,417,687 A | 5/1995 | Nardella et al. |
| 5,422,926 A | 6/1995 | Smith et al. |
| 5,426,685 A | 6/1995 | Pellegrino et al. |
| 5,428,658 A | 6/1995 | Oettingger et al. |
| 5,429,582 A | 7/1995 | Williams |
| 5,452,367 A | 9/1995 | Bick et al. |
| 5,484,384 A | 1/1996 | Fearnot |
| 5,503,613 A | 4/1996 | Weinberger |
| 5,506,877 A | 4/1996 | Niklason et al. |
| 5,520,646 A | 5/1996 | D'Andrea |
| 5,526,394 A | 6/1996 | Siczek et al. |
| 5,535,817 A | 7/1996 | Dunne |
| 5,539,797 A | 7/1996 | Heidsieck et al. |
| 5,553,111 A | 9/1996 | Moore et al. |
| 5,562,594 A | 10/1996 | Weeks |
| 5,566,221 A | 10/1996 | Smith et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzki et al. |
| 5,603,991 A | 2/1997 | Kupiecki et al. |
| 5,609,152 A | 3/1997 | Pellegrino et al. |
| 5,611,767 A | 3/1997 | Williams |
| 5,616,114 A | 4/1997 | Thornton et al. |
| 5,621,780 A | 4/1997 | Smith et al. |
| 5,624,395 A | 4/1997 | Mikhail et al. |
| 5,627,869 A | 5/1997 | Andrew et al. |
| 5,653,683 A | 8/1997 | D'Andrea |
| 5,657,362 A | 8/1997 | Giger et al. |
| 5,662,580 A | 9/1997 | Bradshaw et al. |
| 5,668,889 A | 9/1997 | Hara |
| 5,704,926 A | 1/1998 | Sutton |
| 5,706,327 A | 1/1998 | Adamkowski et al. |
| 5,719,952 A | 2/1998 | Rooks |
| 5,720,717 A | 2/1998 | D'Andrea |
| 5,724,400 A | 3/1998 | Swerdloff et al. |
| 5,735,264 A | 4/1998 | Siczek et al. |
| 5,741,253 A | 4/1998 | Michaelson |
| 5,759,173 A | 6/1998 | Preissman et al. |
| 5,769,086 A | 6/1998 | Ritchart et al. |
| 5,782,742 A | 7/1998 | Crocker et al. |
| 5,800,333 A | 9/1998 | Liprie |
| 5,803,895 A | 9/1998 | Kronholz et al. |
| 5,803,912 A | 9/1998 | Siczek et al. |
| 5,818,898 A | 10/1998 | Tsukamoto et al. |
| 5,820,594 A | 10/1998 | Fontirroche et al. |
| 5,820,717 A | 10/1998 | Siegenthaler |
| 5,828,722 A | 10/1998 | Ploetz et al. |
| 5,851,182 A | 12/1998 | Sahadevan |
| 5,863,284 A | 1/1999 | Klein |
| 5,863,285 A | 1/1999 | Coletti |
| 5,872,828 A | 2/1999 | Niklason et al. |
| 5,878,104 A | 3/1999 | Ploetz |
| 5,896,437 A | 4/1999 | Ploetz |
| 5,899,882 A | 5/1999 | Waksman et al. |
| 5,908,406 A | 6/1999 | Ostapchenko et al. |
| 5,913,813 A | 6/1999 | Williams et al. |
| 5,916,143 A | 6/1999 | Apple et al. |
| 5,919,473 A | 7/1999 | Elkhoury |
| 5,924,973 A | 7/1999 | Weinberger |
| 5,931,774 A | 8/1999 | Williams et al. |
| 5,935,098 A | 8/1999 | Blaisdell et al. |
| 5,986,662 A | 11/1999 | Argiro et al. |
| 5,993,972 A | 11/1999 | Reich et al. |
| 6,005,907 A | 12/1999 | Ploetz |
| 6,022,308 A | 2/2000 | Williams |
| 6,022,325 A | 2/2000 | Siczek et al. |
| 6,033,357 A | 3/2000 | Ciezki et al. |
| 6,036,631 A | 3/2000 | McGrath et al. |
| 6,050,930 A | 4/2000 | Teirstein |
| 6,075,879 A | 6/2000 | Roehrig et al. |
| 6,083,148 A | 7/2000 | Williams |
| 6,086,970 A | 7/2000 | Ren |
| 6,091,841 A | 7/2000 | Rogers et al. |
| 6,093,142 A | 7/2000 | Ciamacco, Jr. |
| 6,095,966 A | 8/2000 | Chomenky et al. |
| 6,137,527 A | 10/2000 | Abdel-Malek et al. |
| 6,141,398 A | 10/2000 | He et al. |
| 6,143,013 A | 11/2000 | Samson et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,200,257 B1 | 3/2001 | Winkler |
| 6,216,540 B1 | 4/2001 | Nelson et al. |
| 6,217,565 B1 | 4/2001 | Cohen |
| 6,219,059 B1 | 4/2001 | Argiro |
| 6,233,473 B1 | 5/2001 | Shepherd et al. |
| 6,234,952 B1 | 5/2001 | Liprie |
| 6,243,441 B1 | 6/2001 | Zur |
| 6,251,059 B1 | 6/2001 | Apple et al. |
| 6,256,370 B1 | 7/2001 | Yavuz |
| 6,256,529 B1 | 7/2001 | Holupka et al. |
| 6,267,775 B1 | 7/2001 | Clerc et al. |
| 6,272,207 B1 | 8/2001 | Tang |

(56) References Cited

U.S. PATENT DOCUMENTS

| | | |
|---|---|---|
| 6,282,142 B1 | 8/2001 | Miyawaki |
| 6,289,235 B1 | 9/2001 | Webber et al. |
| 6,292,530 B1 | 9/2001 | Yavus et al. |
| 6,306,074 B1 | 10/2001 | Waksman et al. |
| 6,319,188 B1 | 11/2001 | Lovoi |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,378,137 B1 | 4/2002 | Hassan et al. |
| 6,390,967 B1 | 5/2002 | Forman et al. |
| 6,390,968 B1 | 5/2002 | Harmon |
| 6,390,992 B1 | 5/2002 | Morris et al. |
| 6,398,708 B1 | 6/2002 | Hastings et al. |
| 6,411,836 B1 | 6/2002 | Patel et al. |
| 6,413,203 B1 | 7/2002 | Sahatjian |
| 6,413,204 B1 | 7/2002 | Winkler et al. |
| 6,415,015 B2 | 7/2002 | Nicolas et al. |
| 6,416,457 B1 | 7/2002 | Urick et al. |
| 6,416,492 B1 | 7/2002 | Nielson |
| 6,442,288 B1 | 8/2002 | Haerer et al. |
| 6,458,069 B1 | 10/2002 | Tam et al. |
| 6,458,070 B1 | 10/2002 | Waksman et al. |
| 6,459,925 B1 | 10/2002 | Nields et al. |
| 6,482,142 B1 | 11/2002 | Winkler et al. |
| 6,501,819 B2 | 12/2002 | Unger et al. |
| 6,512,942 B1 | 1/2003 | Burdette et al. |
| 6,527,693 B2 | 3/2003 | Munro, III et al. |
| 6,540,655 B1 | 4/2003 | Chin et al. |
| 6,556,655 B1 | 4/2003 | Chichereau et al. |
| 6,558,390 B2 | 5/2003 | Cragg |
| 6,579,221 B1 | 6/2003 | Peterson |
| 6,597,762 B1 | 7/2003 | Ferrant et al. |
| 6,605,030 B2 | 8/2003 | Weinberger |
| 6,606,515 B1 * | 8/2003 | Windheuser ...... A61M 25/0097 600/434 |
| 6,607,477 B1 | 8/2003 | Longton et al. |
| 6,610,013 B1 | 8/2003 | Fenster et al. |
| 6,611,575 B1 | 8/2003 | Alyassin et al. |
| 6,615,070 B2 | 9/2003 | Lee |
| 6,616,629 B1 | 9/2003 | Verin et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,673,006 B2 | 1/2004 | Winkler |
| 6,685,618 B2 | 2/2004 | Tam et al. |
| 6,706,014 B2 | 3/2004 | Banik et al. |
| 6,723,052 B2 | 4/2004 | Mills |
| 6,744,848 B2 | 6/2004 | Stanton et al. |
| 6,746,392 B2 | 6/2004 | Stiger et al. |
| 6,748,044 B2 | 6/2004 | Sabol et al. |
| 6,749,555 B1 | 6/2004 | Winkler et al. |
| 6,749,595 B1 | 6/2004 | Murphy |
| 6,751,285 B2 | 6/2004 | Eberhard et al. |
| 6,752,752 B2 | 6/2004 | Geitz |
| 6,758,824 B1 | 7/2004 | Miller et al. |
| 6,770,058 B1 | 8/2004 | Liprie |
| 6,813,334 B2 | 11/2004 | Koppe et al. |
| 6,882,700 B2 | 4/2005 | Wang et al. |
| 6,885,724 B2 | 4/2005 | Li et al. |
| 6,912,319 B1 | 6/2005 | Barnes et al. |
| 6,913,600 B2 | 7/2005 | Valley et al. |
| 6,923,754 B2 | 8/2005 | Lubock |
| 6,940,943 B2 | 9/2005 | Claus et al. |
| 6,955,641 B2 | 10/2005 | Lubock |
| 6,970,531 B2 | 11/2005 | Eberhard et al. |
| 6,978,040 B2 | 12/2005 | Berestov |
| 6,983,754 B1 | 1/2006 | Anderson et al. |
| 6,987,831 B2 | 1/2006 | Ning |
| 6,999,554 B2 | 2/2006 | Mertelmeier |
| 7,098,463 B2 | 8/2006 | Adamovics |
| 7,107,089 B2 | 9/2006 | Lee |
| 7,110,490 B2 | 9/2006 | Eberhard et al. |
| 7,110,502 B2 | 9/2006 | Tsuji |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,171,255 B2 | 1/2007 | Holupka et al. |
| 7,201,715 B2 | 4/2007 | Burdette et al. |
| 7,214,178 B2 | 5/2007 | Lubock |
| 7,245,694 B2 | 7/2007 | Jing et al. |
| 7,315,607 B2 | 1/2008 | Ramsauer |
| 7,319,735 B2 | 1/2008 | Defreitas |
| 7,322,929 B2 | 1/2008 | Lovoi |
| 7,323,692 B2 | 1/2008 | Rowlands et al. |
| 7,404,791 B2 | 7/2008 | Linares et al. |
| 7,407,476 B2 * | 8/2008 | Lubock et al. .................. 600/3 |
| 7,413,539 B2 | 8/2008 | Lubock et al. |
| 7,430,272 B2 | 9/2008 | Jing et al. |
| 7,443,949 B2 | 10/2008 | Defreitas et al. |
| 7,465,268 B2 | 12/2008 | Lubock et al. |
| 7,476,235 B2 | 1/2009 | Diederich et al. |
| 7,497,819 B2 | 3/2009 | White et al. |
| 7,497,820 B2 | 3/2009 | White et al. |
| 7,513,861 B2 | 4/2009 | Klein et al. |
| 7,517,310 B2 | 4/2009 | Lubock et al. |
| 7,609,806 B2 | 10/2009 | Defreitas et al. |
| 7,630,533 B2 | 12/2009 | Ruth et al. |
| 7,662,082 B2 | 2/2010 | White et al. |
| 7,697,660 B2 | 4/2010 | Ning |
| 7,783,006 B2 | 8/2010 | Stewart et al. |
| 7,792,245 B2 | 9/2010 | Hitzke et al. |
| 7,869,563 B2 | 1/2011 | Defreitas et al. |
| 7,885,382 B2 | 2/2011 | Stewart et al. |
| 7,887,476 B2 | 2/2011 | Hermann et al. |
| 8,075,469 B2 | 12/2011 | Lubock et al. |
| 8,079,946 B2 | 12/2011 | Lubock et al. |
| 8,137,256 B2 | 3/2012 | Cutrer et al. |
| 8,192,344 B2 | 6/2012 | Lubock et al. |
| 8,277,370 B2 | 10/2012 | Quick |
| 8,287,442 B2 | 10/2012 | Quick |
| 8,565,374 B2 | 10/2013 | Defreitas et al. |
| 2001/0016725 A1 | 8/2001 | Valley et al. |
| 2001/0038681 A1 | 11/2001 | Stanton et al. |
| 2001/0038861 A1 | 11/2001 | Hsu et al. |
| 2001/0049464 A1 | 12/2001 | Ganz |
| 2001/0051669 A1 | 12/2001 | McGhee |
| 2002/0012450 A1 | 1/2002 | Tsujii |
| 2002/0026090 A1 * | 2/2002 | Kaplan et al. .................. 600/7 |
| 2002/0045893 A1 | 4/2002 | Lane et al. |
| 2002/0050986 A1 | 5/2002 | Inoue et al. |
| 2002/0055666 A1 | 5/2002 | Hunter et al. |
| 2002/0075997 A1 | 6/2002 | Unger et al. |
| 2002/0095114 A1 | 7/2002 | Palasis |
| 2002/0156342 A1 * | 10/2002 | Burton et al. .................. 600/29 |
| 2002/0177804 A1 | 11/2002 | Saab |
| 2003/0018272 A1 | 1/2003 | Treado et al. |
| 2003/0073895 A1 | 4/2003 | Nields et al. |
| 2003/0095624 A1 | 5/2003 | Eberhard et al. |
| 2003/0144570 A1 | 7/2003 | Hunter et al. |
| 2003/0153803 A1 | 8/2003 | Harmon |
| 2003/0194050 A1 | 10/2003 | Eberhard |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0212373 A1 * | 11/2003 | Hall ................ A61M 25/0668 604/263 |
| 2003/0215120 A1 | 11/2003 | Uppaluri et al. |
| 2004/0039437 A1 | 2/2004 | Sparer et al. |
| 2004/0054366 A1 | 3/2004 | Davison et al. |
| 2004/0066884 A1 | 4/2004 | Hermann Claus et al. |
| 2004/0066904 A1 | 4/2004 | Eberhard et al. |
| 2004/0087827 A1 | 5/2004 | Lubock |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0116767 A1 | 6/2004 | Lebovic et al. |
| 2004/0147800 A1 * | 7/2004 | Barber et al. .................. 600/7 |
| 2004/0171986 A1 | 9/2004 | Tremaglio, Jr. et al. |
| 2004/0215048 A1 | 10/2004 | Lubock |
| 2004/0260142 A1 | 12/2004 | Lovoi |
| 2004/0267157 A1 | 12/2004 | Miller et al. |
| 2005/0016771 A1 | 1/2005 | Mayes et al. |

(56) References Cited

U.S. PATENT DOCUMENTS

| | | |
|---|---|---|
| 2005/0049521 A1 | 3/2005 | Miller et al. |
| 2005/0061771 A1 | 3/2005 | Murphy |
| 2005/0063509 A1 | 3/2005 | DeFreitas et al. |
| 2005/0078797 A1 | 4/2005 | Danielsson et al. |
| 2005/0080313 A1 | 4/2005 | Stewart et al. |
| 2005/0101823 A1 | 5/2005 | Linares et al. |
| 2005/0105679 A1 | 5/2005 | Wu et al. |
| 2005/0113681 A1 | 5/2005 | DeFreitas |
| 2005/0113715 A1 | 5/2005 | Schwindt et al. |
| 2005/0124843 A1 | 6/2005 | Singh |
| 2005/0129172 A1 | 6/2005 | Mertelmeier |
| 2005/0135555 A1 | 6/2005 | Claus et al. |
| 2005/0135664 A1 | 6/2005 | Kaufhold et al. |
| 2005/0182286 A1 | 8/2005 | Lubock |
| 2005/0226375 A1 | 10/2005 | Eberhard et al. |
| 2005/0240073 A1 | 10/2005 | Apffelstaedt et al. |
| 2005/0240074 A1 | 10/2005 | Lubock |
| 2005/0267320 A1* | 12/2005 | Barber et al. ............ 600/7 |
| 2005/0277577 A1 | 12/2005 | Hunter et al. |
| 2006/0020156 A1 | 1/2006 | Shukla |
| 2006/0020256 A1 | 1/2006 | Bell et al. |
| 2006/0030784 A1 | 2/2006 | Miller et al. |
| 2006/0074288 A1 | 4/2006 | Kelly |
| 2006/0098855 A1 | 5/2006 | Gkanatsios |
| 2006/0100475 A1 | 5/2006 | White et al. |
| 2006/0116546 A1 | 6/2006 | Eng |
| 2006/0129062 A1 | 6/2006 | Nicoson et al. |
| 2006/0136051 A1 | 6/2006 | Furst et al. |
| 2006/0155209 A1 | 7/2006 | Miller et al. |
| 2006/0167416 A1 | 7/2006 | Mathis et al. |
| 2006/0173233 A1 | 8/2006 | Lovoi |
| 2006/0173235 A1 | 8/2006 | Lim et al. |
| 2006/0205992 A1 | 9/2006 | Lubock et al. |
| 2006/0291618 A1 | 12/2006 | Eberhard et al. |
| 2007/0005003 A1 | 1/2007 | Patterson et al. |
| 2007/0030949 A1 | 2/2007 | Jing et al. |
| 2007/0036265 A1 | 2/2007 | Jing et al. |
| 2007/0055144 A1 | 3/2007 | Neustadter et al. |
| 2007/0076844 A1 | 4/2007 | Defreitas et al. |
| 2007/0106108 A1 | 5/2007 | Hermann et al. |
| 2007/0142694 A1 | 6/2007 | Cutrer et al. |
| 2007/0167665 A1* | 7/2007 | Hermann et al. ............ 600/3 |
| 2007/0167666 A1 | 7/2007 | Lubock et al. |
| 2007/0191667 A1 | 8/2007 | Lubock et al. |
| 2007/0223651 A1 | 9/2007 | Wagenaar et al. |
| 2007/0225600 A1 | 9/2007 | Weibrecht |
| 2007/0242800 A1 | 10/2007 | Jing |
| 2007/0270627 A1 | 11/2007 | Cutrer et al. |
| 2008/0009659 A1* | 1/2008 | Smith et al. ............ 600/3 |
| 2008/0019581 A1 | 1/2008 | Gkanatsios |
| 2008/0045833 A1 | 2/2008 | Defreitas |
| 2008/0057298 A1 | 3/2008 | Finley |
| 2008/0064915 A1 | 3/2008 | Lubock |
| 2008/0086083 A1 | 4/2008 | Towler |
| 2008/0091055 A1 | 4/2008 | Nguyen et al. |
| 2008/0101537 A1 | 5/2008 | Sendai |
| 2008/0112534 A1 | 5/2008 | DeFreitas et al. |
| 2008/0130979 A1 | 6/2008 | Ren |
| 2008/0177127 A1* | 7/2008 | Allan et al. ............ 600/7 |
| 2008/0188705 A1 | 8/2008 | Lubock et al. |
| 2008/0221384 A1 | 9/2008 | Chi Sing et al. |
| 2008/0221444 A1 | 9/2008 | Ritchie et al. |
| 2008/0228023 A1 | 9/2008 | Jones et al. |
| 2008/0228024 A1 | 9/2008 | Jones et al. |
| 2008/0228025 A1 | 9/2008 | Quick |
| 2008/0228150 A1 | 9/2008 | Jones et al. |
| 2008/0281142 A1 | 11/2008 | Lubock et al. |
| 2008/0281143 A1 | 11/2008 | Lubock et al. |
| 2008/0287801 A1 | 11/2008 | Magnin et al. |
| 2009/0003519 A1 | 1/2009 | Defreitas |
| 2009/0010384 A1 | 1/2009 | Jing |
| 2009/0030259 A1 | 1/2009 | Quick |
| 2009/0080594 A1 | 3/2009 | Brooks |
| 2009/0080602 A1 | 3/2009 | Brooks |
| 2009/0093821 A1* | 4/2009 | Edmundson ............ 606/108 |
| 2009/0124845 A1 | 5/2009 | Lubock et al. |
| 2009/0135997 A1 | 5/2009 | Defreitas |
| 2009/0156880 A1 | 6/2009 | Allan et al. |
| 2009/0156882 A1 | 6/2009 | Chi Sing et al. |
| 2009/0171157 A1 | 7/2009 | Diedrich et al. |
| 2009/0188098 A1 | 7/2009 | Acosta et al. |
| 2009/0198095 A1 | 8/2009 | Acosta et al. |
| 2009/0213987 A1 | 8/2009 | Stein et al. |
| 2009/0268865 A1 | 10/2009 | Ren |
| 2009/0296882 A1 | 12/2009 | Gkanatsios |
| 2009/0304147 A1 | 12/2009 | Jing et al. |
| 2010/0048977 A1* | 2/2010 | Sing et al. ............ 600/6 |
| 2010/0054400 A1 | 3/2010 | Ren |
| 2010/0086188 A1 | 4/2010 | Ruth |
| 2010/0150306 A1 | 6/2010 | Defreitas et al. |
| 2010/0195882 A1 | 8/2010 | Ren |
| 2010/0204534 A1 | 8/2010 | Damarati |
| 2010/0204535 A1 | 8/2010 | Damarati |
| 2010/0226475 A1 | 9/2010 | Smith |
| 2010/0286465 A1 | 11/2010 | Benson |
| 2010/0290585 A1 | 11/2010 | Eliasson |
| 2011/0069809 A1 | 3/2011 | Defreitas et al. |
| 2012/0071705 A1 | 3/2012 | Lubock et al. |

FOREIGN PATENT DOCUMENTS

| | | |
|---|---|---|
| EP | 0536440 | 4/1993 |
| EP | 0642766 | 3/1995 |
| EP | 0693293 | 1/1996 |
| EP | 0719571 | 7/1996 |
| EP | 775467 | 5/1997 |
| EP | 0853957 | 7/1998 |
| EP | 0867200 | 9/1998 |
| EP | 0982001 | 3/2000 |
| EP | 1051990 | 11/2000 |
| EP | 1070514 | 1/2001 |
| EP | 1402922 | 3/2004 |
| EP | 1428473 | 6/2004 |
| EP | 1541188 | 6/2005 |
| EP | 1618924 | 1/2006 |
| EP | 1759637 | 3/2007 |
| JP | 10137250 | 5/1998 |
| JP | 2001120561 | 5/2001 |
| RU | 2177350 | 12/2001 |
| WO | WO 90/05485 | 5/1990 |
| WO | WO 92/10932 | 7/1992 |
| WO | WO 93/09724 | 5/1993 |
| WO | WO 9520241 | 7/1995 |
| WO | WO 9712540 | 4/1997 |
| WO | WO 97/19723 | 6/1997 |
| WO | WO 97/45053 | 12/1997 |
| WO | WO 98/16903 | 4/1998 |
| WO | WO 9815315 | 4/1998 |
| WO | WO 99/11325 | 3/1999 |
| WO | WO 99/33515 | 7/1999 |
| WO | WO 9934869 | 7/1999 |
| WO | WO 99/42163 | 8/1999 |
| WO | WO 01/14011 | 7/2000 |
| WO | WO 00/51484 | 9/2000 |
| WO | WO 01/43826 | 6/2001 |
| WO | WO 01/58346 | 8/2001 |
| WO | WO 02/09599 | 2/2002 |
| WO | WO 02/069862 | 9/2002 |
| WO | WO 03/020114 | 3/2003 |
| WO | WO 2004/043531 | 5/2004 |
| WO | WO 2004/043535 | 5/2004 |
| WO | WO 2005/037363 | 4/2005 |
| WO | WO 2005039655 | 5/2005 |
| WO | WO 2005039665 | 5/2005 |
| WO | WO 2005/051197 | 6/2005 |
| WO | WO 2005/067442 | 7/2005 |
| WO | WO 2005110230 | 11/2005 |
| WO | WO 2005112767 | 12/2005 |
| WO | WO 2006/055830 | 5/2006 |
| WO | WO 2006/058160 | 6/2006 |
| WO | WO 2007/027831 | 3/2007 |
| WO | WO 2007/143560 | 12/2007 |

(56) References Cited

FOREIGN PATENT DOCUMENTS

| WO | WO 2008/067557 | 6/2008 |
|---|---|---|
| WO | WO 09/079170 | 6/2009 |

OTHER PUBLICATIONS

"Filtered Back Projection," (NYGREN) published May 8, 2007; URL:http://web.archive.org/web/19991010131715/http://www.owlnet.rice.edu/-.about.e1ec539/Projects97/cult/node2.html, 2 pgs.
"Lorad Selenia" Document B-BI-SEO US/Intl (May 2006), copyright Hologic 2006, 12 pgs.
"Variable shield for radiation-therapy sourcewire and centering catheter", Research disclosure, Mason Publications, Hampshire, GB, vol. 438, No. 48, Oct. 2000, XP007126916, 1 page.
Abstracts of the 11th International Conference on Brain tumor Research and Therapy Oct. 31-Nov. 3, 1995, Silverado Country Club and Resort, Napa, California, Journal of Neuro-Oncology 28, p. 72, 1996, 2 pages all together.
Akagi, Y, et al.,"Optimum Fractionation for High-Dose-Rate Endoesophageal Brachytherapy Following External Irradiation of Early State Esophageal Cancer", Int. J. Radiation Oncology Biol. Phys., vol. 43, 1999, pp. 525-530, Elsevier Science, Inc.
Ashpole et al., "A New Technique of Brachytherapy for Malignant Gliomas with Caesium-137: A New Method Utilizing a Remote Afterloading System," Clinical Oncology, 1990, vol. 2, pp. 333-337.
Astrahan, Melvin A., PhD et al., "Optimization of Mammosite therapy", Int. J. Radiation Oncology Biol. Phys, vol. 58, No. 1, pp. 220-232, 2004.
Bowsher. W. G., et al., "Update on Urology-Prostate Cancer. 4-Treatment of Local Disease". European Journal of Surgical Oncology. 1995 pp. 679-682. vol. 21. No. 6.
Chan, Heang-Ping et al., "ROC study of the effect of stereoscopic imaging on assessment of breast lesions", Medica Physics, vol. 32, No. 4, Apr. 2005, 7 pgs.
Cole, Elodia, et al., "The Effects of Gray Scale Image Processing on Digital Mammography Interpretation Performance", Academic Radiology, vol. 12, No. 5, pp. 585-595, May 2005.
Cuttino, L. W., et al.,"CT-Guided Multi-Catheter Insertion Technique for Partial Breast Brachytherapy: Reliable Target Coverage and Dose Homogeneity", Brachy1herapy 4, 2005, pp. 10-17, Elsevier.
Das, R. K., et al., "3D-CT-Based High-Dose-Rate Breast Brachytherapy Implants: Treatment Planning and Quality Assurance", Int. J. Radiation Oncology Biol. Phys. 2004, pp. 1224-1228, vol. 59, No. 4, Elsevier Inc.
Debicki, M. P., et al., "Localized Current Field Hyperthermia in Carcinoma of The Cervix: 3-D Computer Simulation of SAR Distribution". International Journal of Hyperthermia. 1999. pages 427-440. vol. 15. No. 5.
Demanes, D. J . et al., "The Use and Advantages of a Multichannel Vaginal Cylinder in High-Dose-Rate Brachytherapy". Int. J. Radiation Oncology Biol. Phys. (1999). pp. 211-219. vol. 44. No. 1. Elsevier Science Inc.
Dempsey, J. F. et al., "Dosimetric Properties of a Novel Brachytherapy Balloon Applicator for the Treatment of Malignant Brain-Tumor Resection-Cavity Margins", Int. J. Radiation Oncology Biol. Phys., May 1998, pp. 421-429, vol. 42. No. 2. Elsevier.
Devic et al., "Advantages of Inflatable Multichannel Endorectal Applicator in the Neo-Adjuvant Treatment of Patients With Locally Advanced Rectal Cancer With HOR Brachytherapy", Journal of Applied Clinical Medical Physics, Spring 2005, pp. 44-49, vol. 6, No. 2.
Digital Clinical Reports, Tomosynthesis, GE Brochure 98-5493, Nov. 1998, 8 pgs.
Edmundson,Gregory K. et al., "Dosimetric Characteristics of the Mammosite RTS, a New Breast Brachytherapy Applicator", Int. J. Radiation Oncology Biol. Phys., vol. 52, No. 4, pp. 1132-1139, 2002.

Federica Pediconi et al., "Color-coded automated signal intensity-curve for detection and characterization of breast lesions: Preliminary evaluation of a new software for MR-based breast imaging", International Congress Series 1281 (2005) 1081-1086.
Fowler, J. E., "Brief Summary of Radiobiological Principles in Fractionated Radiotherapy", Seminars in Radiation Oncology, Jan. 1992, pp. 16-21, vol. 2, No. 1, W. B. Saunders Company.
Friedman, M, et al., "A New Technic for the Radium Treatment of Carcinoma of the Bladder", Presented at the Thirty-fourth Annual Meeting of the Radiological Society of North America, Dec. 5-10, 1948, pp. 342-362.
Friedman, M, et al., "Irradiation of Carcinoma of the Bladder by a Central Intracavitary Radium or Cobalt 60 Source (The Walter Reed Technique)", Presented at the Annual Meeting of the American Radium Society, 1955, pp. 6-31.
Garipagaoglu, M. et al., "Geometric and Dosimetric Variations of ICRU Bladder and Rectum Reference Points in Vaginal Cuff Brachytherapy Using Ovoids", Int. J. Radiation Oncology Biol. Phys. 2004, pp. 1607-1615. Elsevier Inc.
Gaspar, L. E., et al., "Esophageal Brachytherapy", Principles and Practice of Brachytherapy, 1997, pp. 305-321, Futrua Publishing Company, Inc., Armouk, New York.
Glasgow, G. P., et al. "Remote Afterloading Technology", AAPM Report No. 41, 1993, pp. i-vi and 1-107, American Institute of Physics, Inc., 116 pgs.
Gutin, P.H. et al., "A coaxial catheter system for afterloading radioactive sources for the interstitial irradiation of brain tumors", J. Neurosur, vol. 56, pp. 734-735, 1982.
Hall, J. W., et al., "Histologic Changes in Squamous-Cell Carcinoma of the Mouth and Oropharynx Produced by Fractionated External Roentgen Irradiation", Radiological Society of North America, 1948, pp. 318-350, Mar. 3, 1950.
Harada, T, et al., "Transcystoscopic Intracavitary irradiation for Carcinoma of the Bladder: Technique and Preliminary Clinical Results", The Journal of Urology, Oct. 1987, pp. 771-774, vol. 138, No. 4, The Williams & Wilkins Co.
Harper, Paul V., "Some Therapeutic Applications of Radioisotopes", Journal of the Mississippi State Medical Association, Oct. 1966, vol. VII, pp. 526-533.
Hewitt, C. B., et al., "Intracavitary Radiation in the Treatment of Bladder Tumors", The Journal of Urology, vol. 107, Apr. 1972, pp. 603-606, The Williams & Wilkins Co.
Hewitt, C. B., et al., "Update on Intracavitary Radiation in the Treatment of Bladder Tumors", The Journal of Urology; Official Journal of The American Urological Association, Inc., 1981, pp. 323-325, vol. 126 September, The Williams & Wilkins Co.
Hieshima,G. B., et al. "A Detachable Balloon for Therapeutic Transcatheter Occlusions 1", Technical Notes, Jan. 1981, pp. 227-228, vol. 138.
Hine, G. J., et al., "Isodose Measurements of Linear Radium Sources in Air and Water by Means of an Automatic Isodose Recorder", The American Journal of Roentgenology and Radium Therapy, 1950, pp. 989-998, vol. 64, No. 6, The Societies.
Hoshino, T., "Brain Tumor Research Center", Abstracts of the 11th Conference on Brain Tumor Research and Therapy, Journal of Neuro-Oncology 28, 1996, pp. 31-113.
Johannesen, T.B. et al, "Intracavity Fractioned Balloon Brachytherapy in Glioblastoma", Acta Neurochir (Wien) (1999) 141: 127-133.
Kaufman, N., "Remote Afterloading Intraluminal Brachytherapy in the Treatment of Rectal, Rectosigmoid, and Anal Cancer: A Feasibility Study", International Journal of Radiation Oncology, Biology, Physics, Sep. 1989, pp. 663-668, vol. 17, Issue 3, Pergamon Press pic.
Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.
Kolotas., C. et al., "CT Guided Interstitial High Dose Rate Brachytherapy for Recurrent Malignant Gliomas". The British Journal of Radiology. 72. (1999), pp. 805-808.
Kuettel, M. R. et al.. "Treatment of Female Urethral Carcinoma in Medically Inoperable Patients Using External Beam Irradiation and

(56) References Cited

OTHER PUBLICATIONS

High Dose Rate Intracavitary Brachytherapy", The Journal of Urology. May 1997, pp. 1669-1671, vol. 157, The American Urological Association, Inc.
Lewis, J, et al., "Intracranial Brachytherapy Using a High Dose Rate Microselectron", Northern Centre for Cancer Treatment, Dept. of Neurosciences, Regional Medical Physics Department, Newcastle General Hospital, Newcastle Upon Tyne, UK, Radiation and Oncology, vol. 39, Supplement 1, May 1996, pp. 45-45, 1 page, p. 179.
Low-Beer, B. V. A., "Radioisotope Therapy", "The Clinical Use of Radioactive Isotopes", 1950, pp. 284-349, Charles C. Thomas, Publisher, Springfield, Illinois, U.S.A., See pp. 343-349.
Low-Beer, B. V. A., "The Therapeutic Use of Radioactive Isotopes", "Practical Therapeutics", Dec. 1954, pp. 69-87, vol. X, No. 6.
Mammographic Accreditation Phantom, http://www.cirsinc.com/pdfs/015cp.pdf, (2006), 2 pgs.
Marshall V. F., et al., "Current Clinical Problems Regarding Bladder Tumors", Symposium on Bladder Tumors, 1956, pp. 543-550, 9/3/May-Jun, J.B. Lippincott Co, Etc.
Micheletti, E., et al., "High-Dose-Rate Brachytherapy for Poor-Prognosis, High-Grade Glioma: (Phase II) Preliminary Results", Tumori, 1996, pp. 339-344.
Muller, J. H., "Radiotherapy of Bladder Cancer by Means OF Rubber Balloons Filled In Situ With solutions of a Radioactive Isotope (Co60)", Cancer, A Journal of the American Cancer Society, Jul.-Aug. 1955, pp. 1035-1043, vol. 8, No. 4, J.B. Lippincott Company, Philadelphia.
Nag, S, "Modern Techniques of Radiation Therapy for Endometrial Cancer", Clinical Obstetrics and Gynecology, Sep. 1996, pp. 728-744, vol. 39, No. 3, Lippincott-Raven Publishers.
Nag, S., et al., "Perineal Template Interstitial Barchytherapy Salvage for Recurrent Endometrial Adenocarcinoma Metastatic to the Vagina", Necologic Oncology 66, 1997, pp. 16-19, Article No. G0974722, Academic Press.
Nag, S., et al., "Remote Controlled High Dose Rate Brachytherapy", Critical Reviews in Oncology/Hematology 22, 1996, pp. 127-150, Elsevier Science Ireland Ltd.
Nag, S., et al., "The Future of High Dose Rate Brachytherapy", High Dose Rate Brachytherapy: A Textbook, 1994, pp. 447-453, Futura Publishing Company, Inc., Armonk, New York 10504.
Nath, Ph.D. et al., "Development of an 241 Am Applicator for Intracavitary Irradiation of Gynecologic Cancers", I.J. Radiation Oncology Biol. Phys., May 1988, vol. 14, p. 969-978.
Pernot, M., "Combined Surgery and Brachytherapy in the Treatment of Some Cancers of the Bladder (Partial Cystectomy and Interstitial Iridium—192)", Radiotherapy & Oncology, 1996, pp. 115-120, Elsevier Science Ireland Ltd.
Rotman, M., et al., "The Intracavitary Applicator in Relation to Complications of Pelvic Radiation—The Ernst System", Int. J. Radiation Oncology Biol. Phys., 1978, pp. 951-956, vol. 4, Pergamon Press Inc.
Russel, A.H., et al, "Intracavitary Irradiation for Carcinoma of the Urinary Bladder: Rationale, Technique, and Preliminary Results", Int. J. Radiation Oncology. Phys., 1984, pp. 215-219, vol. 10, Pergamon Press Ltd.
Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.
Slevin. N. J. et al., "Intracavitary Radiotherapy Boosting for Nasopharynx Cancer", The British Journal of Radiology, 70, Apr. 1997, pp. 412-414.
Smith, A., "Fundamentals of Breast Tomosynthesis", White Paper, Hologic Inc., WP-00007, Jun. 2008, 8 pgs.
Sneed. P. K. et al., "Interstitial Brachytherapy Procedures for Brain Tumors", Seminars in Surgical Oncology 1997; 13: 157-166. Wiley-Liss. Inc.
Stubbs, J.B., et al., "Preclinical Evaluation of a Novel Device for Delivering Brachytherapy to the Margins of Resected Brain Tumor Cavities", J. Neurosurg 96, Feb. 2002, pp. 335-343, vol. 96.
Sylvester, J., et al., "Interstitial Implantation Techniques in Prostate Cancer", Journal of Surgical Oncology 1997; 66: 65-75. Wiley-Liss. Inc.
Symon et al., "Individual Fraction Optimization vs. First Fraction Optimization for Multichannel Applicator Vaginal Cuff High-Dose-Rate Brachytherapy", pp. 211-215, Brachytherapy 5 (2006), Elsevier.
Tan, L. T. et al., "Radical Radiotherapy for Carcinoma of the Uterine Cervix Using External Beam Radiotherapy and a Single Line Source Brachytherapy Technique: The Clatterbridge Technique", The British Journal of Radiology, 70, Dec. 1997, pp. 1252-1258.
Tanderup et al. "Multi-Channel Intracavitary Vaginal Brachytherapy Using Three-Dimensional Optimization of Source Geometry", Radiation & Oncology Journal of the European Society for Therapeutic Radiology and Oncology, 2004, pp. 81-85, Radiotherapy and Oncology 70 (2004), Elsevier Ireland Ltd.
Vicini, F. A., et al, "Dose-Volume Analysis for Quality Assurance of Interstitial Brachytherapy for Breast Cancer", Int. J. Radiation Oncology Biol. Phys., vol. 45, 1999, pp. 803-810, Elsevier Science Inc.
Voung, T, et al., "High-Dose-Rate Endorectal Brachytherapy in the Treatment of Loacally Advanced Rectal Carcinoma: Technical Aspects", Brachytherapy 4, 2005, pp. 230-235, Elsevier.
Walton, R. J., "Therapeutic Uses of Radioactive Isotopes in the Royal Cancer Hospital", The British Journal of Radiology, 1950, pp. 559-599, William Heinemann, Publisher.
Walton, R. J., et al., Radioactive Solution (24Na and 82 Br) in the Treatment of Carcinoma of the Bladder:, British Medical Bulletin, 1952, pp. 158-165, Medical Dept., The British Council.
Wang, C. C., "Carcinoma of the Nasopharynx", Radiation Therapy of Head and Neck Neoplasms, 1997, pp. 257-280, Chapter 10, Wiley-Liss, Inc.
Wheeler, F.W. et al. (2006), "Micro-Calcification Detection in Digital Tomosynthesis Mammography", Proceedings of SPIE, Conf-Physics of Semiconductor Devices, Dec. 11, 2001 to Dec. 15, 2001, Delhi, SPIE, US, vol. 6144, Feb. 13, 2006, 12 pgs.
Wolf, C. D., et al., "A Unique Nasopharynx Brachytherapy Technique", Official Journal of the American Association of Medical Dosimetrists, 1990, pp. 133-136, vol. 15, Issue No. 3., Pergamon Press.
Wu, Tao et al., "Tomographic mammography using a limited number of low-dose cone-beam images", Medical Physics, AIP, Melville, NY, vol. 30, No. 3, Mar. 1, 2003, pp. 365-380.
"DuPont Teflon PFA HP Plus", XP007904995:retrieved from the internet: URL: http://www2.dupont.com/Teflon_Industrial/en_US/assets/downloads/h88800.pdf; retrieved on Jun. 19, 2008, by Authorized Officer in International Application PCT/US2008/003364, 4 pgs.
Xu, Z., et al., "Calculation of Dose Distribution Near an Innovative Concentric Balloon Catheter for Endovascular Brachytherapy", Cardiovascular Radiation Medicine 2, 2000, pp. 26-31, Elsevier Science Inc.
Yin, W., "Brachtherapy of Carcinoma of the Esophagus in China, 1970-1974 and 1982-1984", Brachytherapy HOR and LOR, May 4-6, 1989, pp. 52-56.

* cited by examiner

ORIENTING A BRACHYTHERAPY APPLICATOR

FIELD OF THE INVENTION

This disclosure generally relates to the field of brachytherapy and, more particularly to orienting a brachytherapy treatment catheter within a treatment cavity, such as a breast lumpectomy cavity.

BACKGROUND OF THE INVENTION

Malignant tumors are often treated by surgical resection to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it. Radiation therapy can be administered through one of several methods, or a combination of methods, including external-beam radiation, stereotactic radiosurgery, and brachytherapy. The term "brachytherapy," as used herein, refers to radiation therapy delivered by a source of therapeutic rays inserted into the body at or near a tumor or other proliferative tissue disease site.

A typical breast brachytherapy radiation treatment involves insertion of an applicator by a surgeon. A brachytherapy applicator may typically include a flexible catheter shaft with an inflatable balloon mounted on its distal end. One or more dosing lumens extend within the catheter shaft and into the balloon. The catheter shaft is inserted into a body so that the balloon is positioned within a resected cavity. The balloon is subsequently inflated and radioactive material, for example in the form of one or more radioactive seeds, is loaded into one or more of the dosing lumens for radiation delivery. The brachytherapy catheter system is removed upon completion of treatment. In single lumen brachytherapy treatment devices the dosing lumen is positioned along a central axis of the balloon such that substantially symmetrical isodose profiles may be achieved during treatment, i.e., a radiation dose of equal intensity is delivered to the tissue surrounding the balloon. In multi-lumen brachytherapy treatment devices one or more lumens are offset from the central axis within the balloon such that asymmetrical isodose profiles may be achieved during treatment, i.e., a radiation dose of greater intensity is delivered to certain areas of tissue surrounding the balloon in comparison to other areas, which receive a dose of lesser intensity. Proper orientation of the treatment device is desirable for delivering an asymmetric isodose profile. A physician may be able to make minor adjustments by applying direct rotational force to the shaft by hand. However, the catheter shaft may be ill-suited to transmitting torque. For example, a flexible shaft may initially twist in response to rotational force and then unpredictably untwist as applied resistance to twist increases and torque exceeds friction between the applicator and tissue. As a result, it is difficult to precisely orient the applicator.

SUMMARY

In accordance with an aspect of the invention a device for orienting a brachytherapy applicator implanted in a treatment cavity includes an elongated body defining an open proximal end, an open distal end, and an open channel between the proximal and distal ends. The channel slidably receives at least a portion of a brachytherapy applicator during use. The device may include a manually engageable gripping element. The gripping element may be located at the proximal end of the elongated body, and be operable to constrict at least a portion of the channel to prevent rotational movement between the elongated body and a portion of a brachytherapy applicator inserted into the channel. The device may also include at least one engaging element disposed on a portion of the elongated body for releasably engaging at least one corresponding engaging element on the brachytherapy applicator, wherein the elongated body and brachytherapy applicator are prevented from rotating relative to each other when the at least one engaging element of the elongated body engages the at least one corresponding engaging element of the brachytherapy applicator.

In accordance with another aspect of the invention a brachytherapy system includes a brachytherapy applicator for insertion into a treatment cavity and a device for orienting the brachytherapy applicator upon insertion into a treatment cavity. The brachytherapy applicator includes a flexible shaft defining a proximal end, a distal end and a shaft lumen extending between the proximal end distal ends, an inflatable member disposed about the distal end of the shaft, at least one dosing lumen extending through the shaft lumen and into the inflatable member, and at least one first engaging element disposed on a portion of the shaft. The device for orienting the brachytherapy applicator includes an elongated body defining an open proximal end, an open distal end, and an open channel between the proximal and distal ends adapted for slidably receiving at least a portion of the flexible shaft. The device may also include a manually engageable gripping element at the proximal end of the elongated body, the gripping element operable to constrict at least a portion of the channel around at least a portion of the flexible shaft to prevent rotational movement between the elongated body and the brachytherapy applicator. Furthermore, the device may include at least one second engaging element adapted for releasably engaging the at least one first engaging element of the brachytherapy applicator. The device and brachytherapy applicator are prevented from rotating relative to each other when the at least one first engaging element of the elongated body engages the at least one second engaging element of the brachytherapy applicator.

In accordance with another aspect of the invention a method for orienting a brachytherapy applicator with the device described above includes the steps of positioning the elongated body on the shaft and controlling axial or rotational movement of the applicator via the device. This may be accomplished by positioning the device relative to the applicator such that the first and second engaging elements engage one another, thereby preventing rotational movement of the shaft and elongated body relative to each other. Applying a force to the gripping element and constricting at least a portion of the channel around at least a portion of the shaft prevents rotational movement of the shaft and elongated body relative to each other. An operator may then perform one or more of (i) axially moving the orienting device and simultaneously axially moving the brachytherapy device relative to a target tissue area of the treatment cavity and (ii) rotating the orienting device and simultaneously rotating the brachytherapy device relative to a target tissue area of the treatment cavity.

The invention provides a cost effective and easily operable way to orient a brachytherapy applicator. The device enables 1:1 rotation with reduced shaft twist and helps avoid stick-slip by securing a segment of the applicator shaft against twist and spreading the torque load. Tabs reduce reliance on friction between fingers and device or shaft. Advantageously, the device can be mounted and removed without removing the applicator from the treatment cavity. It is also advantageous that the orienting device is an "external tool" that engages the flexible shaft of the brachytherapy applicator externally about its outer surface as opposed to an "internal tool" which must be inserted down an internal shaft lumen to engage an internal engagement structure. Such an external configuration reduces or eliminates the need to incorporate more costly and complex internal structures within the tight diametrical confines of the applicator, which are required to accommodate an internal orienting device.

These and other features, aspects, and advantages of the disclosed embodiments will become better understood with regard to the following description, appended claims, and accompanying drawings.

Although the drawings represent embodiments of the present invention, the drawings are not necessarily to scale and certain features may be exaggerated in order to better illustrate and explain the present invention. The exemplification set out herein illustrates certain embodiments of the invention, in one, or more forms, and such exemplifications are not to be construed as limiting the scope of the invention in any manner.

DETAILED DESCRIPTION

Figure 1:
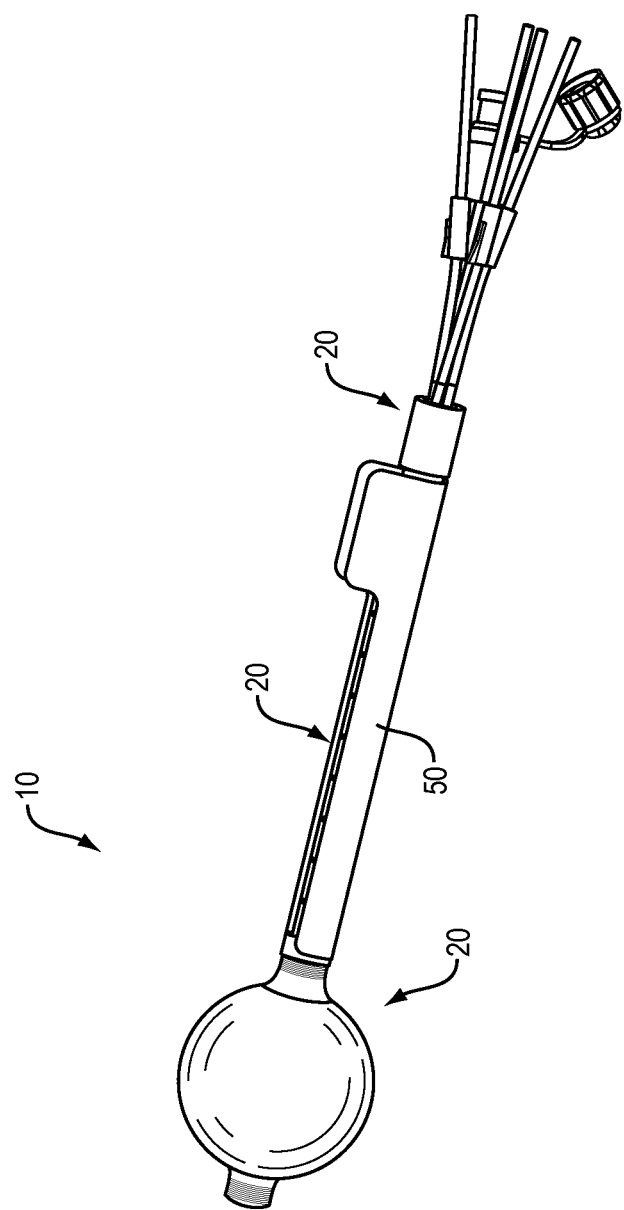
FIG. 1 is an isometric view of a brachytherapy system described in the present disclosure.

Referring to FIG. 1, a brachytherapy system is indicated generally by the reference numeral 10. The system 10 includes a brachytherapy applicator 20, such as the brachytherapy applicator described in U.S. Patent Application Publication No. 2010/0204534, entitled "Flexible Multi-Lumen Brachytherapy Device", which is hereby in incorporated by reference in its entirety as part of the present disclosure, and a device adapted for orienting a brachytherapy applicator 50 (hereinafter referred to as the "orienting device")

Figure 2A:
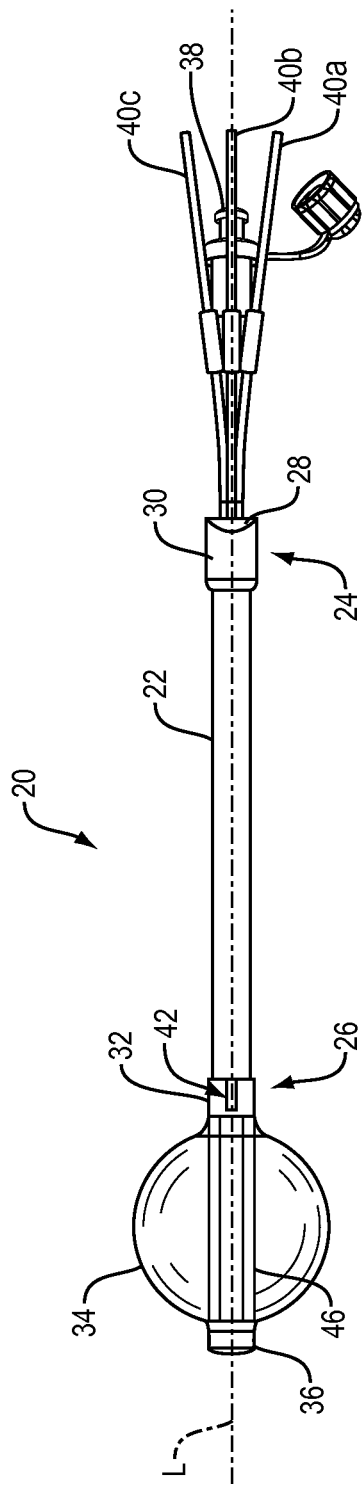
FIG. 2A is top elevation view of the brachytherapy applicator of the system shown in FIG. 1.
Figure 2B:
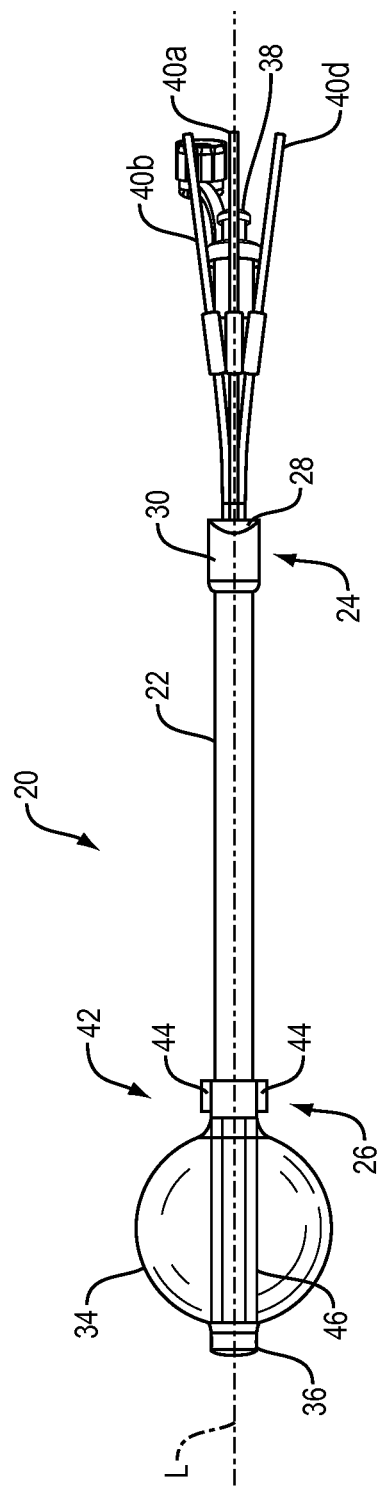
FIG. 2B is side elevation view of the brachytherapy applicator of the system shown in FIG. 1.

FIGS. 2A and 2B are top and side elevation views of an embodiment of the brachytherapy applicator 20 which may be used in the system 10 (FIG. 1). The applicator 20 comprises a flexible shaft 22 or catheter body defining a proximal end 24, a distal end 26 and a shaft lumen 28 extending between the proximal end distal ends. A proximal hub 30 is disposed circumferentially about the proximal end of the shaft and a distal hub 32 is disposed circumferentially about the distal end of the shaft. An inflatable member 34, such as a balloon, is disposed about the distal end 26 of the shaft 22. The applicator further includes a tip member 36, which may form an outboard portion of the distal end of the shaft 22 or, alternatively, may be indirectly coupled to the shaft 22 in which case the tip member 36 is spaced distally from the distal end of the shaft. In one embodiment, the inflatable member 34 is located between the proximal hub 30 and the tip member 36. And in some such embodiments, the inflatable member is located between the distal hub 32 and the tip member 36 as illustrated, for example, in FIGS. 2A-2B. The applicator has a rotational position indicator mark on the shaft which may be aligned with one of the lumens.

Figure 7A:
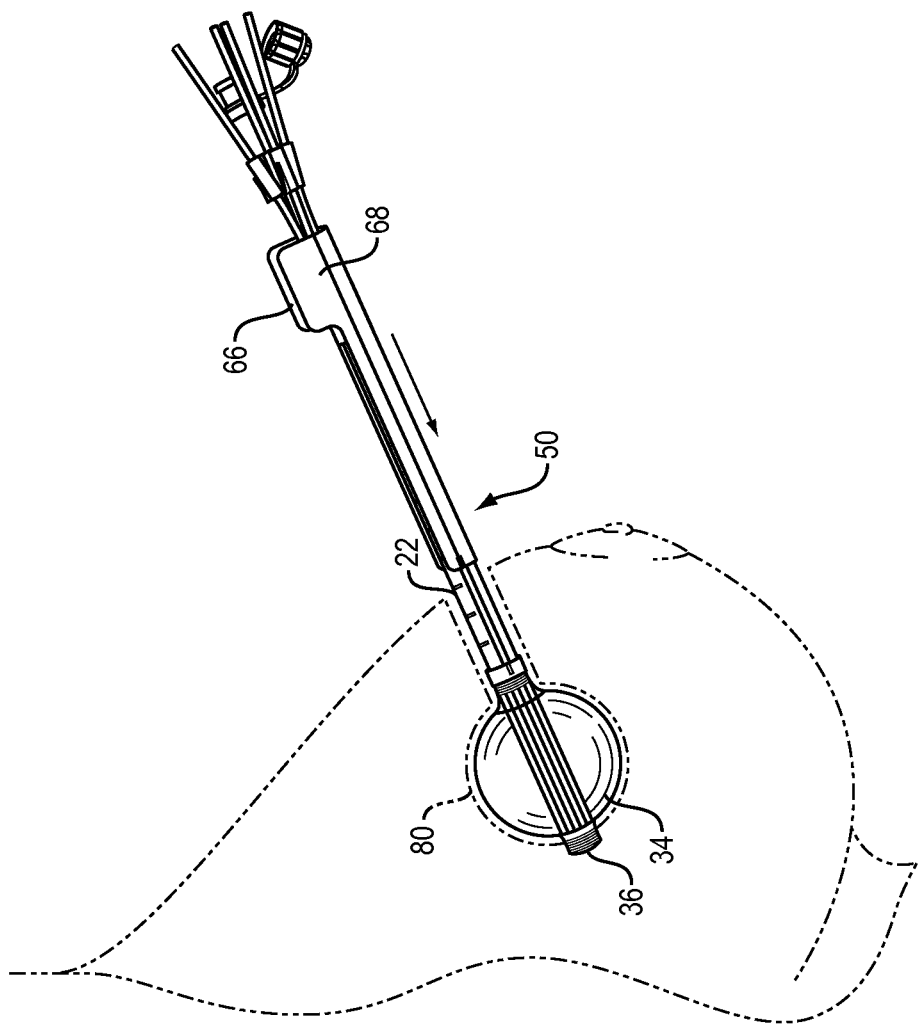
FIG. 7A is a partial isometric view showing the brachytherapy applicator of the system shown in FIG. 1 implanted within a treatment cavity. The orienting device is inserted on the shaft and being slid forward to engage the shaft.

The applicator 20 further includes a flexible inflation lumen 38, which channels fluid into and out of the inflatable member 34 to inflate and deflate the inflatable member as required. When inflated, inflatable member 34 helps to maintain the position of the applicator 20 with respect to a treatment cavity (see e.g. FIG. 7 A) into which the applicator was implanted. At least one flexible dosing lumen 40a extends through the shaft lumen 28 and into the inflatable member 34. The dosing lumen 40a providing provides a conduit sized to accommodate and position one or more radiation sources, such as a radioactive seed. In one embodiment, the applicator 20 includes at least four dosing lumens 40a-d. To help secure the dosing lumens, a positioning hub 46 affixed within the inflatable member 34 between the tip member 26 and distal hub 32 may be included. The positioning hub defines grooves or channels into which corresponding lumens are secured to maintain their position inside the inflatable member relative to the central longitudinal axis L of the applicator 20.

Figure 5A:
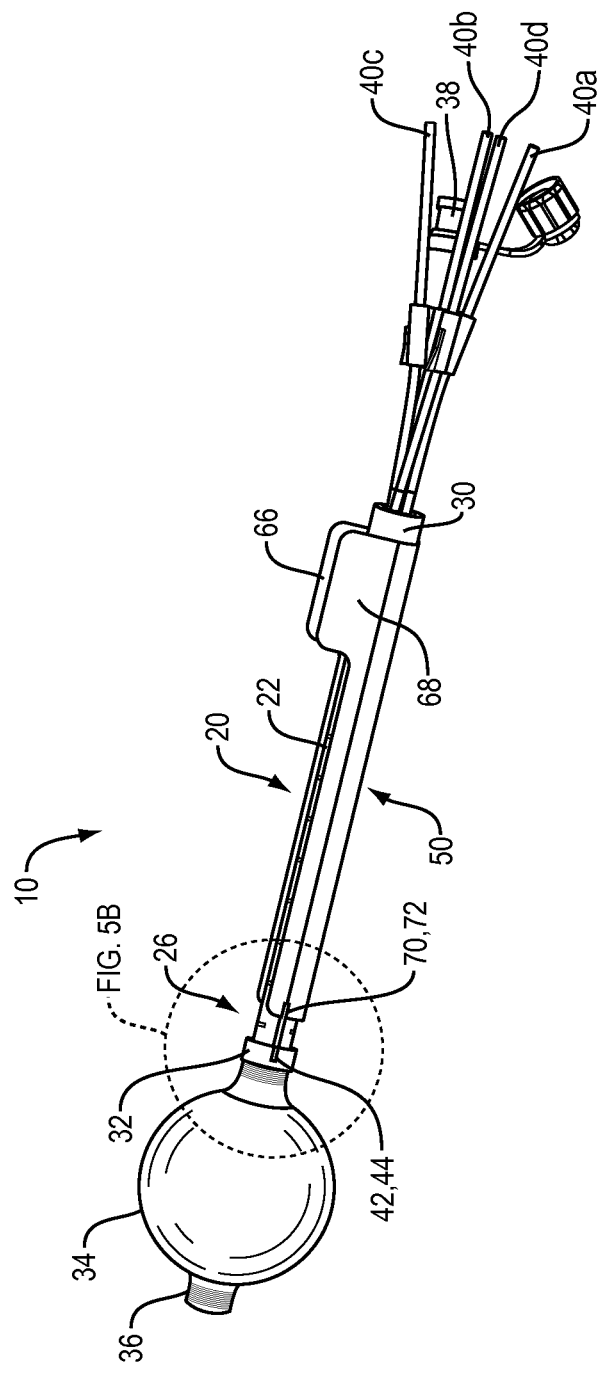
FIG. 5A is an isometric view of the system of claim 1 showing the orienting device mounted on the shaft of the applicator but disengaged from the shaft.
Figure 5B:
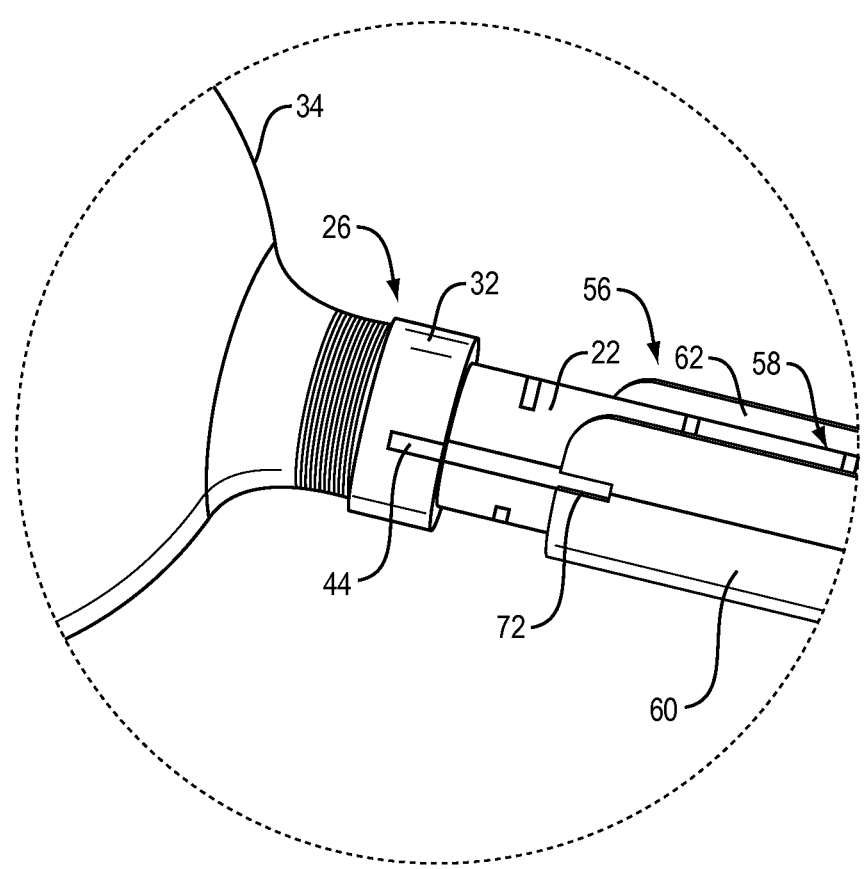
FIG. 5B is a close-up view of the distal ends of the applicator shaft and orienting device shown in FIG. 5A

The applicator 20 further includes at least one engaging member 42 (see e.g. FIGS. 2B and 5B). In one embodiment, the at least one engaging member is a set of protrusions 44. The protrusions 44 extend outward from the distal hub 32 and are spaced approximately 180 degrees apart relative to the central longitudinal axis of the applicator 20. It should be noted however that the protrusions 44 could extend from other locations along the shaft 22 and the angular relationship between the protrusions 44 about the longitudinal axis may be more or less than 180 degrees, as long as the protrusions 44 are able to align with corresponding slots 72 (described below) on the orienting device 50.

Figure 3:
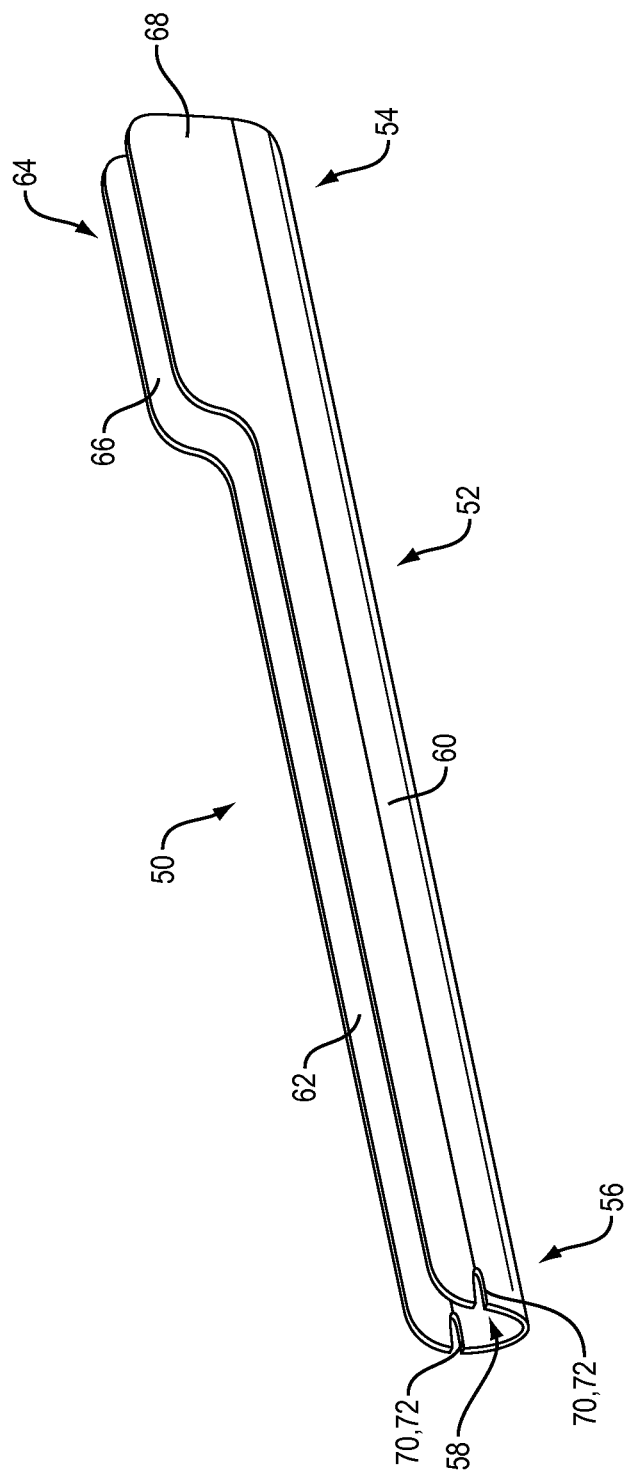
FIG. 3 is an isometric view of the orienting device of the system shown in FIG. 1.
Figure 4:
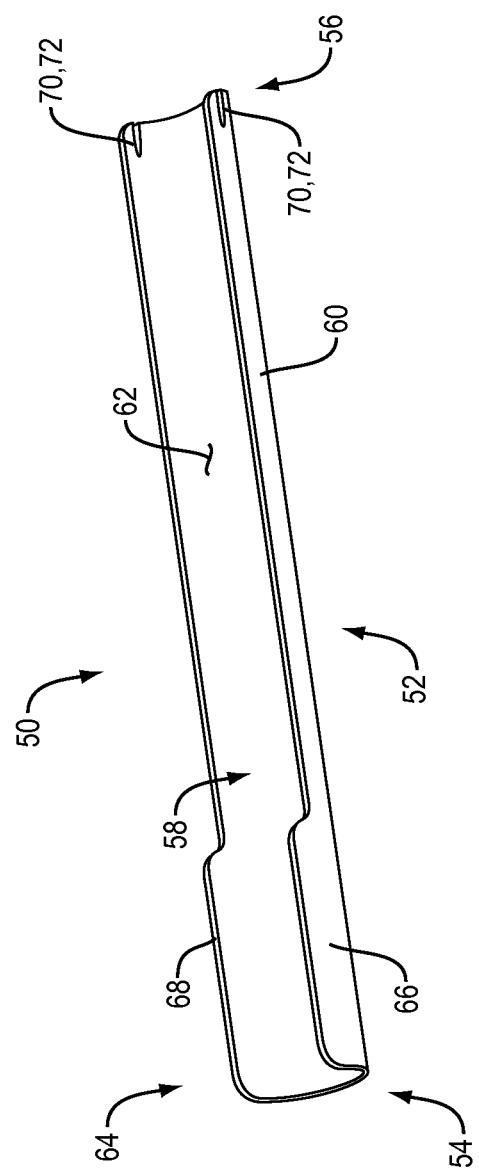
FIG. 4 is another isometric view of the orienting device of the system shown in FIG. 1.

Referring now to FIGS. 3 and 4, an embodiment of the orienting device 50 which may be used in the system 10 (FIG. 1) will be described in further detail. The device 50 comprises an elongated body 52 defining an open proximal end 54, an open distal end 56, and an open channel 58 extending longitudinally between the proximal and distal ends. The channel 58 is adapted for slidably receiving at least a portion of the shaft or catheter body of a brachytherapy applicator, such as the flexible shaft 22 of the above-described brachytherapy applicator 20 depicted in FIGS. 2A-B. The channel defines an outer surface 60 and an inner surface 62. In one embodiment, the channel 58 is approximately semi-cylindrical or u-shaped; however, the channel 58 may take on other shapes suitable for accommodating the particular shaft or catheter body of a brachytherapy applicator.

The device 50 includes one or more features which enable a physician to control movement of the brachytherapy applicator. For example, the device may be used to control axial, rotational, or both axial and rotational movement of the applicator 20. The features may include a mechanism which secures the device 50 to the applicator 20 such that the applicator moves in response to movement of the device 50. Independent control may be provided such that axial control is disabled while the applicator is rotationally positioned. Operation of the mechanism may be reversible such that the device 50 may be disengaged from the applicator 20, e.g., after the applicator has been properly positioned. The device may also be used multiple times to reposition the applicator by repeatedly engaging and disengaging the device and applicator.

In the illustrated embodiment the channel 58 is capable of gripping or otherwise frictionally engaging an inserted shaft or catheter body, such as the shaft 22 of the above-described brachytherapy applicator 20. In such instances the channel 58 defines a relaxed state and a constricted state. When in the relaxed state, the inner surface 52 of the channel does not frictionally engage the inserted shaft 22 so that the elongated body 52 may slide axially in at least one direction relative to the shaft 22. When in the constricted state, at least a portion of an inner surface 62 of the channel frictionally engages at least a portion of an outer surface of an inserted shaft 22 so that the elongated body 52 is not axially or rotationally slidable relative to the shaft 22.

A manually engageable gripping element 64 provides an actuator operable to transition or otherwise move the channel between the relaxed and constricted states. The manually engageable gripping element 64 resides at or about the proximal end 54 of the elongated body 52. The gripping element 64 may form a portion or appendage of the elongated body (i.e. the gripping element 64 and elongated body 52 may be a single piece), or the gripping element 64 may be a separate component attached to the elongated member 52. As noted above, the gripping element 64 is operable to transition or otherwise move the channel between the relaxed and constricted states. In one embodiment, the gripping element 64 includes a pair of opposing tabs or surfaces 66, 68 adapted to move or otherwise flex or bend toward each upon application of a lateral force on each tab. The forces are directed inward in a squeezing type motion applied by the operator to substantially simultaneously transition the channel 58 from its relaxed state to its constricted state. Releasing the gripping element (i.e. ceasing the application of the lateral forces on the tabs) will return the channel 28 to its relaxed state; hence, the channel is biased in its relaxed state.

Referring now to FIGS. 3, 5A-B and 6A-B, in the illustrated embodiment the orienting device 50 further includes at least one engaging element 70 located about the distal end 56 of the elongated body and adapted for releasably engaging the at least one (corresponding) engaging element 42 on the brachytherapy applicator 20. When the at least one engaging element 70 of the elongated body engages the at least one corresponding engaging element 42 of the brachytherapy applicator (or vice versa), the orienting device 50 and brachytherapy applicator 20 are prevented from rotating relative to each other (i.e. the device 50 and applicator 20 can only rotate in unison). In one embodiment, the at least one engaging element 70 is at least one slot 72 defined by a portion of the distal end 56 of the elongated member 52. The at least one slot 72 is adapted for receiving a corresponding protrusion 44 extending from a portion of the brachytherapy applicator 20. In the illustrated embodiment, the at least one engaging element includes two slots 72 angularly spaced approximately 180 degrees relative to each other about a central longitudinal axis of the elongated body 52. It should be noted that the slots 72 could reside at other locations about the elongated member and the angular relationship between the slots 72 about the longitudinal axis may be more or less than 180 degrees, as long as the slots 72 are able to align with their corresponding protrusions 44.

The orienting device 50 described above may be made from a polymer such as polypropylene, fluorinated ethylene propylene (FEP), nylon or polyethylene block amide (PEBA). However, as one skilled in the art would recognize, the device 50 may be made from a number of suitable materials including, but not limited to, additional polymers, metals and combinations thereof.

Figure 5C:
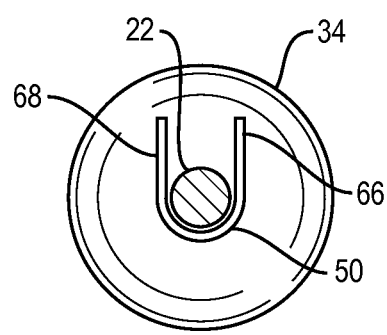
FIG. 5C is a partial front end view of the system of claim 1 showing the shaft received within the channel and channel is in its relaxed state.

Having thus described the system 10 and its primary components, an example method of use will now be described. With the brachytherapy applicator 20 having been surgically implanted into a treatment cavity, such as a resected breast lumpectomy cavity 80 shown in FIGS. 7A-B, the orienting device 50 is inserted onto the shaft 22 of the applicator 20. When properly inserted, the shaft 22 will rest in the channel 58 of the device 10 and the channel will be in its relaxed state (FIG. 5C), allowing the elongated body 52 of the device to slide axially on the shaft 22. The physician (or operator) then positions the elongated body 52 on the shaft 22 so that the engaging elements 42, 70 on the shaft and elongated body align and then engage one another. In the illustrated embodiment, the protrusions 44 on the distal hub 32 of the applicator 20 and the corresponding slots 72 in the distal end 56 of the elongated body 52 of the device 50 form the engaging elements 42, 70. Accordingly, the physician will align the protrusions 42 and slots 70 and (see e.g. FIGS. 5A-B and 7A) and then slide the elongated body 52 distally along the shaft 22 until the protrusions enter and are received by (i.e. engage) the slots (see e.g. FIGS. 6A-B and 7B). When the protrusions are received by the slots, the applicator 20 and orienting device 50 are releasably engaged, thereby preventing rotational movement of the applicator 20 and device 50 relative to each other (i.e. the applicator 20 and device can only rotate in unison; individual rotation of either the applicator 20 or shaft is not permitted).

Figure 6A:
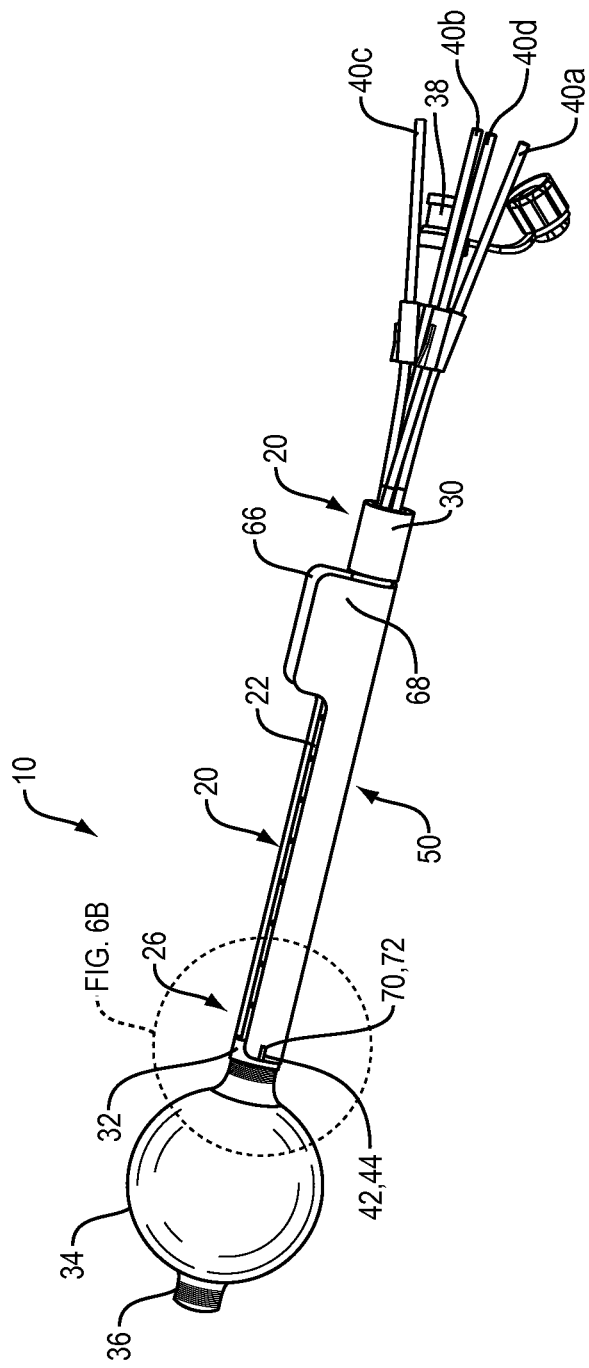
FIG. 6A is an isometric view of the system of claim 1 showing the orienting device mounted on the shaft of the applicator and engaged with the shaft.
Figure 6B:
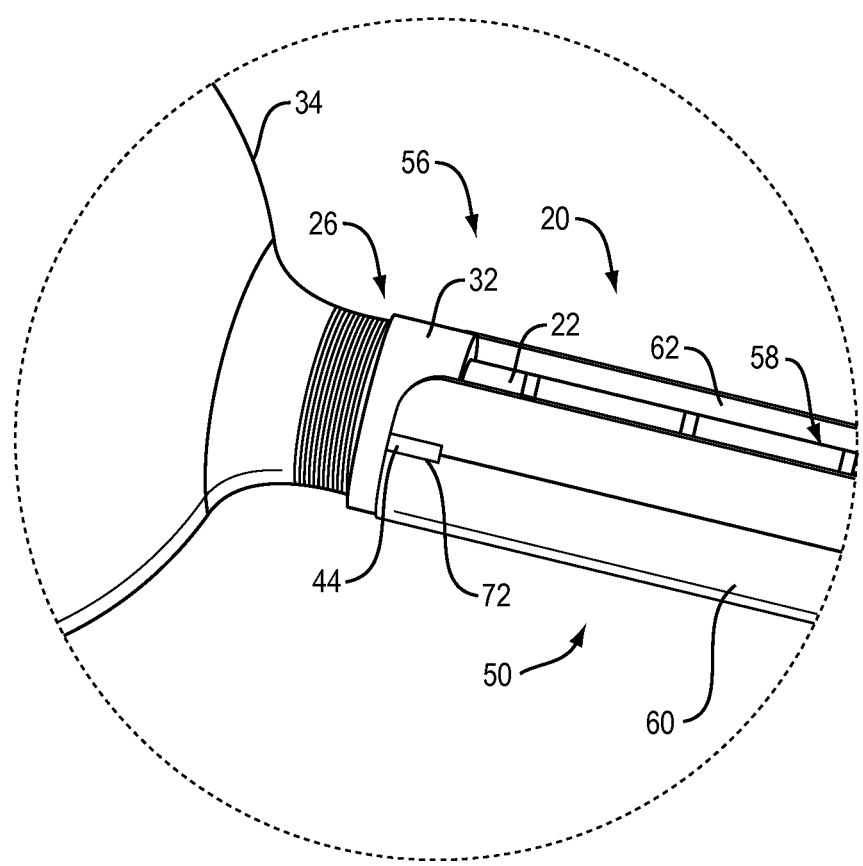
FIG. 6B is a close up view of the distal ends of the applicator shaft and orienting device shown in FIG. 6A
Figure 6C:
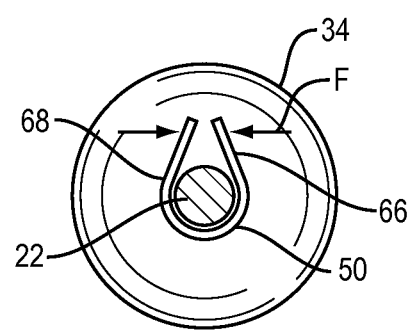
FIG. 6C is a partial front end view of the system of claim 1 showing the shaft received within the channel and channel is in its constricted state.
Figure 7B:
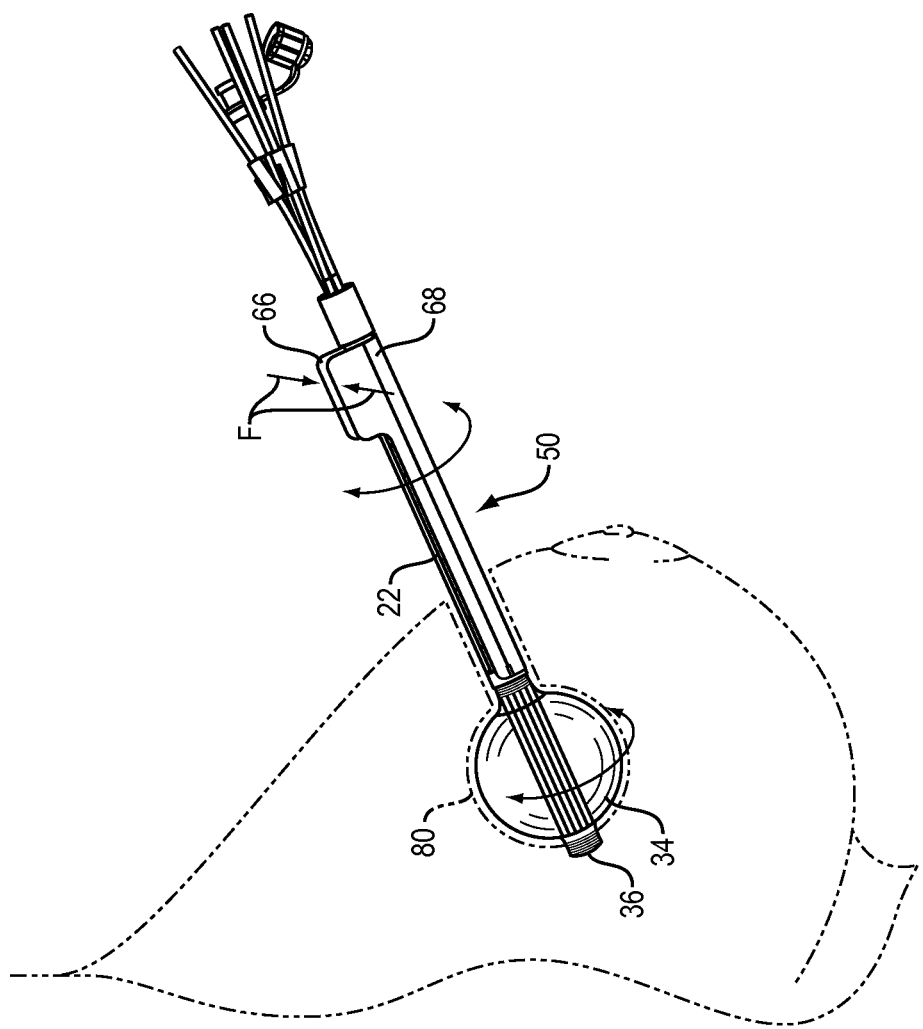
FIG. 7B is a partial isometric view showing the brachytherapy applicator of the system shown in FIG. 1 implanted within a treatment cavity. The orienting device is engaged with shaft so that the applicator and orienting device may rotate and translate in unison.

As shown in FIG. 7B, with the engaging members 42, 70 engaged the physician then applies a force F to the gripping element 64 to transition the channel 58 of device 50 from its relaxed state (FIG. 5C) to its constricted state (FIG. 6C) as described above. In the illustrated embodiment, the gripping element 64 comprises a set of tabs 66, 68. Accordingly, the physician will apply a lateral squeezing force to the tabs 66, 68, moving the tabs toward each other and substantially simultaneously transitioning the channel 58 from its relaxed state to its constricted state. In the constricted state, at least a portion of the channel 58 constricts around at least a portion of the shaft 22, thereby preventing axial and rotational movement of the applicator 20 and orienting device relative to each other. With the applicator 20 and device properly secured, the physician will then perform at least one of the following functions to orient and position the applicator 20 as desired within the treatment 80 and, in particular, orient and position the applicator 20 relative to a target tissue area (not shown) in the treatment cavity. If axial movement is required, the physician will axially move the orienting device 50, which substantially simultaneously axially moves the brachytherapy applicator 20. If angular or rotational movement is desired, the physician will rotate the orienting device 50, which substantially simultaneously rotates the brachytherapy device 20. It should be noted however that constriction around the distal rigid portion of the shaft resulting from squeezing the proximal tabs may engage the slot features to provide a rigid to rigid connection rather than constricting the whole shaft or flexible portion of the shaft.

As may be recognized by those of ordinary skill in the pertinent art based on the teachings herein, numerous changes and modifications may be made to the above-described and other embodiments of the present invention without departing from the spirit and scope of the invention as defined and/or described in the specification, drawings and appended claims. It should be understood that the embodiments shown and described and all changes, modifications and equivalents that come within the spirit and scope of the invention are desired to be protected. Accordingly, this disclosure is to be taken in an illustrative, as opposed to a limiting sense.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. Further, regarding the methods and processes described herein, it should be understood that although the steps of such methods and processes have been described as occurring according to a certain ordered sequence, such processes could be practiced with the described steps performed in an order other than the order described herein. It further should be understood that certain steps could be performed simultaneously, that other steps (not described) could be added or implied, or that certain steps described herein could be omitted.

What is claimed is:

1. An apparatus for orienting a brachytherapy applicator implanted in a treatment cavity of a body of a patient, the apparatus comprising:
   an elongated body comprising an inner surface and an outer surface and defining an open proximal end, an open distal end, and an open continuous channel extending longitudinally between the proximal and distal ends for slidably receiving at least a portion of the brachytherapy applicator, wherein the channel is at least one of approximately semi-cylindrical, u-shaped, and c-shaped; and
   at least one slot, wherein the at least one slot extends longitudinally from the distal end along only a portion of the elongated body, such that the at least one slot is defined by each of the outer surface and the inner surface and the distal end of the elongated body, wherein the at least one slot is configured to secure the elongated body to a corresponding engaging element on an outer surface feature of the brachytherapy applicator such that the brachytherapy applicator moves without twisting in response to movement of the elongated body.

2. The apparatus of claim 1 further including a manually engageable gripping element at the proximal end of the elongated body, the gripping element operable to constrict at least a portion of the channel to prevent rotational movement between the elongated body and the at least a portion of the brachytherapy applicator inserted into the channel.

3. The apparatus of claim 2 wherein the manually engageable gripping element includes a pair of opposing tabs adapted to move toward each other upon application of a lateral force on each tab to constrict the at least a portion of the channel.

4. The apparatus of claim 2 wherein the channel is defined by (i) a relaxed state where the elongated body is axially slidable in at least one direction relative to an inserted shaft or catheter body of the brachytherapy applicator and (ii) a constricted state which inhibits an inserted shaft or catheter body of the brachytherapy applicator from moving rotationally relative to the elongated body, the gripping element operable to move the channel between the relaxed and constricted states.

5. The apparatus of claim 4 wherein at least a portion of an inner surface of the channel frictionally engages at least a portion of the outer surface of an inserted shaft or catheter body of the brachytherapy applicator when the channel is in the constricted state.

6. The apparatus of claim 2 wherein the gripping element is one of (i) part of the elongated body and (ii) a separate component attached to the elongated body.

7. The apparatus of claim 1 wherein the at least one slot includes two slots angularly spaced approximately 180 degrees relative to each other about a central longitudinal axis of the elongated body.

8. The apparatus of claim 1 wherein the channel defines an opening for receiving a shaft of the brachytherapy applicator.

9. The apparatus of claim 1, wherein the at least one slot comprises:
   a first slot extending longitudinally from the distal end, wherein the first slot is defined by each of the outer surface and the inner surface and the distal end of the elongated body; and
   a second slot extending longitudinally from the distal end, wherein the second slot is defined by each of the outer surface and the inner surface and the distal end of the elongated body.

10. A brachytherapy system comprising:
    a brachytherapy applicator adapted for insertion into a treatment cavity, the applicator including:
    a flexible shaft defining a proximal end, a distal end and a shaft lumen extending between the proximal end and the distal end;
    an inflatable member disposed about the distal end of the shaft; and
    at least one dosing lumen extending through the shaft lumen and into the inflatable member; and
    a device for orienting the brachytherapy applicator upon insertion into a treatment cavity, the device including:
    an elongated body comprising an inner surface and an outer surface and defining an open proximal end, an open distal end, and
    an open continuous channel extending longitudinally between the proximal end and the distal end of the elongate body, wherein the channel is adapted for slidably receiving at least a portion of the flexible shaft, wherein the open channel is at least one of approximately semi-cylindrical, u-shaped, and c-shaped; and at least one slot, wherein the at least one slot extends longitudinally from the distal end along only a portion of the elongated body, such that the at least one slot is defined by each of the outer surface and the inner surface and the distal end of the elongated body, wherein the at least one slot is configured to secure the elongated body to an corresponding engaging element on an outer surface of the applicator such that the applicator moves without twisting in response to movement of the elongated body.

11. The system of claim 10, further comprising a manually engageable gripping element at the proximal end of the elongated body, the gripping element operable to constrict at least a portion of the channel around at least a portion of the flexible shaft to prevent rotational movement between the elongated body and the brachytherapy applicator.

12. The apparatus of claim 1 wherein the manually engageable gripping element includes a pair of opposing tabs adapted to move toward each other upon application of a lateral force on each tab to constrict the at least a portion of the channel.

13. The apparatus of claim 10, wherein the at least one slot comprises:

a first slot extending longitudinally from the distal end, wherein the first slot is defined by each of the outer surface and the inner surface and the distal end of the elongated body; and a second slot extending longitudinally from the distal end, wherein the second slot is defined by each of the outer surface and the inner surface and the distal end of the elongated body.

* * * * *